US008551005B2

(12) United States Patent
Baruch

(10) Patent No.: US 8,551,005 B2
(45) Date of Patent: Oct. 8, 2013

(54) MONITORING RESPIRATORY VARIATION OF PULSE PRESSURE

(76) Inventor: Robert A. Baruch, Ellicott City, MD (US)

( * ) Notice: Subject to any disclaimer, the term of this patent is extended or adjusted under 35 U.S.C. 154(b) by 1666 days.

(21) Appl. No.: 11/955,843

(22) Filed: Dec. 13, 2007

(65) Prior Publication Data

US 2009/0156945 A1    Jun. 18, 2009

(51) Int. Cl.
*A61B 5/08* (2006.01)
(52) U.S. Cl.
USPC .......................................... 600/484; 600/125
(58) Field of Classification Search
None
See application file for complete search history.

(56) References Cited

U.S. PATENT DOCUMENTS

| | | | | |
|---|---|---|---|---|
| 4,137,910 | A | 2/1979 | Murphy | 128/2.05 R |
| 4,883,353 | A | 11/1989 | Hausman et al. | 356/41 |
| 5,144,951 | A | 9/1992 | Uematsu et al. | 128/633 |
| 5,178,151 | A | 1/1993 | Sackner | 128/672 |
| 5,769,082 | A | 6/1998 | Perel | 128/671 |
| 6,440,078 | B1 | 8/2002 | Curiel et al. | 600/481 |
| 6,537,225 | B1 | 3/2003 | Mills | 600/481 |
| 6,776,764 | B2 | 8/2004 | Pinsky | 600/481 |
| 7,056,292 | B2 | 6/2006 | Hutchinson | 600/485 |
| 7,209,780 | B2 | 4/2007 | Pfeiffer et al. | 600/431 |
| 2003/0083582 | A1 | 5/2003 | Hirsh | |
| 2003/0167010 | A1 | 9/2003 | Pinsky | |
| 2004/0158163 | A1 | 8/2004 | Cohen et al. | 600/508 |
| 2004/0249297 | A1 | 12/2004 | Pfeiffer et al. | 600/526 |
| 2005/0187481 | A1 | 8/2005 | Hatib et al. | 600/485 |
| 2005/0267379 | A1 | 12/2005 | Pfeiffer et al. | 600/526 |
| 2006/0047213 | A1 | 3/2006 | Gavriely et al. | |
| 2007/0032732 | A1 | 2/2007 | Shelley et al. | 600/504 |
| 2007/0088222 | A1 | 4/2007 | Berkow et al. | 600/485 |
| 2007/0089744 | A1 | 4/2007 | Wiese | 128/204.23 |
| 2007/0179386 | A1 | 8/2007 | Michard et al. | 600/485 |
| 2007/0191724 | A1 | 8/2007 | Hirsh | 600/523 |

OTHER PUBLICATIONS

Yoon et al., Nonconstrained Blood Pressure Measurement by Photoplethysmography, J. Optical Society of Korea, vol. 10, No. 2, Jun. 2006, pp. 91-95.*
Parati et al., Spectral Analysis of Blood Pressure and Heart Rate Variability in Evaluating Cardiovascular Regulation, Hypertension. 1995;25:1276-1286.*
Attinger et al., Use of Fourier Series for the Analysis of Biological Systems, Biophysical Journal vol. 6 1966.*
International Search Report and Written Opinion dated May 15, 2009 issued in corresponding PCT application No. PCT/US2008/013695, 13 pages.
J. Redling et al. "Noninvasive Cardiac Output Estimation: A Preliminary Study", Biological Cybernetics, No. 77; Aug. 1997; pp. 111-122.

(Continued)

*Primary Examiner* — Jim Ketter
*Assistant Examiner* — Reza Ghafoorian
(74) *Attorney, Agent, or Firm* — Snyder, Clark, Lesch & Chung, LLP

(57) ABSTRACT

A monitoring device may include a display, an input device to receive patient-related data, and logic. The logic may determine the pulse pressure of the patient based on the patient-related data, calculate a respiratory variation of the pulse pressure of the patient, and generate a first value based on the respiratory variation of the pulse pressure of the patient and a mean pulse pressure of the patient. The logic may also output the first value to the display. The logic may update the first value in a continuous, real-time or near real-time manner.

22 Claims, 5 Drawing Sheets

(56) References Cited

OTHER PUBLICATIONS

R. Mukkamala et al. "Continuous Cardiac Output Monitoring by Peripheral Blood Pressure Waveform Analysis", Computers in Cardiology, No. 30; 2003; pp. 255-258.

M. Aboy et al., "A Novel Algorithm to Estimate the Pulse Pressure Variation Index ΔPP", IEEE Transactions on Biomedical Engineering, vol. 51, No. 12; Dec. 2004; pp. 2198-2203.

D. Austin et al., "A Novel Approach to Pulse Pressure Variation Estimation", Proceedings of the 28th IEEE EMBS Annual International Conference; Aug. 2006; pp. 1391-1393.

F. Michard et al., "Using Heart-Lung Interactions to Assess Fluid Responsiveness During Mechanical Ventilation"; Critical Care vol. 4, No. 5, Sep. 2000; pp. 282-289.

F. Michard et al., "Relation Between Respiratory Changes in Arterial Pulse Pressure and Fluid Responsiveness in Septic Patients with Acute Circulatory Failure", American Journal of Respiratory and Critical Care Medicine, vol. 162; Jul. 2000, pp. 134-138.

A. Kramer et al., "Pulse Pressure Variation Predicts Fluid Responsiveness Following Coronary Artery Bypass Surgery", American College of Chest Physicians, 126/5; Nov. 2004; pp. 1563-1568.

Pulsion Medical Systems, PiCCO—Technology; "Intelligent Diagnosis and Therapy Management Trend-Setting Monitoring for the Patient's Benefit"; Aug. 2006; 24 pages.

Pulsion Medical Systems, PiCCO—Technology; "Normal Values and Decision Model" product data, Sep. 2006; 2 pages.

Pulsion Medical Systems, PiCCO plus: "Setup & Method" product data; Dec. 2005; 1 page.

Pulsion Medical Systems, PiCCO plus product information; 2006; pp. 1-65.

\* cited by examiner

MONITORING RESPIRATORY VARIATION OF PULSE PRESSURE

BACKGROUND INFORMATION

Introducing fluids to patients, such as patients in shock, is often the first step in medical treatment. However, not all patients are responsive to fluid. For example, responsiveness to fluid administration may be based on the amount of fluid in the vascular space of the patient. Responsiveness to fluid administration may also be based on how full the heart is before each contraction, referred to as preload or ventricular preload. The relationship between the preload state and contractility of the heart has been described and has been shown graphically via the Starling curve.

For example, FIG. 1 illustrates a Starling curve 100 that depicts the relationship between the ventricular preload state of a patient and stroke volume. Referring to FIG. 1, when the preload state of the patient is relatively low, a small change in preload results in a relatively large increase in stroke volume, as illustrated at position A. In contrast, when the preload state of the patient is relatively high, a small change in preload results in a very small change in stroke volume, as illustrated in position B.

While a patient whose heart is in condition A may benefit from fluid administration, a patient in shock whose heart is in condition B may not benefit and may actually be harmed by fluid administration.

Respiratory variation in the pulse pressure of ventilated patients has been shown to correlate with fluid responsiveness. Current methods to monitor the pre-load sate of the heart and fluid responsiveness include echocardiography and the placement of a Swan-Ganz catheter. The Swan-Ganz catheter is inserted into the patient and is carefully moved to the heart to obtain pressure measurements from different vascular compartments. Thermal dilution is used with the Swan-Ganz catheter to measure cardiac output and stroke volume is calculated by dividing cardiac output by the pulse rate. Stroke volume can then be compared before and after fluid administration to determine the preload state of the heart. A problem with using a Swan-Ganz catheter is that the catheter is very invasive and is difficult to place in many patients, such as pediatric patients.

Other monitoring systems track cardiac output and can provide assessments of fluid responsiveness, but require a large central arterial catheter that places the extremity at risk and is unsuitable for use in many patients, such as children. In addition to being very invasive, current methods aimed at quantifying respiratory variation of the pulse pressure are not performed in a continuous manner that enable medical personnel to receive current information regarding the state of the patient.

DETAILED DESCRIPTION OF PREFERRED EMBODIMENTS

The following detailed description refers to the accompanying drawings. The same reference numbers in different drawings may identify the same or similar elements. Also, the following detailed description does not limit the invention. Instead, the scope of the invention is defined by the appended claims and their equivalents.

Implementations described herein provide for continuously monitoring the respiratory variation of pulse pressure. This information may be used as a measure of the preload state of the patient. Implementations described herein also allow the monitoring to be accomplished in a non-invasive manner or relatively non-invasive manner, thereby resulting in little to no trauma or risk to the patient.

Figure 2:
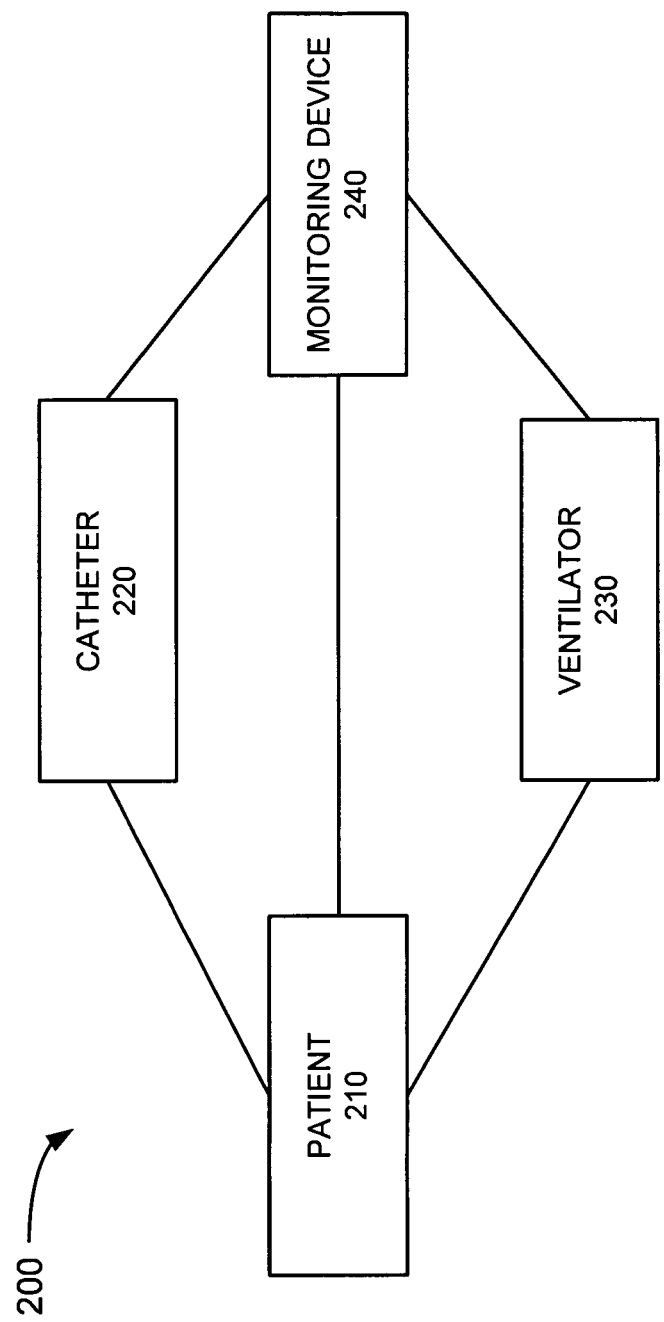
FIG. 2 illustrates an exemplary environment in which systems and methods described herein may be implemented.

FIG. 2 is a block diagram of an exemplary environment in which systems and methods described herein may be implemented. Referring to FIG. 2, environment 200 may include patient 210, catheter 220, ventilator 230 and monitoring device 240.

Patient 210 may represent any person (i.e., an adult or child) that may be in some sort of medical distress, such as in shock or other traumas. Catheter 220 may be a catheter used to measure blood pressure, as described in detail below. In an exemplary implementation, catheter 220 may be an arterial catheter that may be inserted in the wrist or foot of patient 210. Catheter 220 may include a sensor used to measure pressure in the artery. Catheter 220 may also include a transducer to convert the measured pressure into electrical signals corresponding to the measured pressure and provide the electrical signals to monitoring device 240.

Ventilator 230 may be any conventional mechanical ventilator used to assist patient 210 in breathing. In some implementations, ventilator 230 may provide data, such as respiratory rate information, to monitoring device 240.

Monitoring device 240 may include a device used to continuously monitor various parameters associated with patient 210, such as the respiratory variation of the pulse pressure. In an exemplary implementation, monitoring device 240 may receive data from catheter 220 and/or ventilator 230 and determine the respiratory variation of the pulse pressure. This metric may be used to indicate the preload state of patient 210. The respiratory variation of the pulse pressure may be continuously updated to enable medical personnel to monitor the state of patient 210 in a real-time or near real-time manner. This information may then be used to determine, for example, whether to provide a fluid bolus to patient 210. That is, the respiratory variation of the pulse pressure may function to indicate the condition of patient 210 with respect to the Starling curve (FIG. 1) and whether fluid administration would be beneficial or detrimental given the current condition of patient 210.

The exemplary environment 200 illustrated in FIG. 2 is provided for simplicity. It should be understood that a typical environment may include more or fewer devices than illustrated in FIG. 2. For example, catheter 220 is shown as a separate element from the other devices. In other implementations, catheter 220 and/or parts of catheter 220 (e.g., a transducer) may be part of monitoring device 240. In addition, in some implementations, the functions described below as being performed by multiple devices in environment 200 may be performed by a single device. For example, in some implementations, the functions performed by ventilator 230 and monitoring device 240 may be combined into a single device. In addition, in an alternative implementation, ventilator 230 may not be used. That is, patient 210 may not be mechanically ventilated. In addition, in other implementations, catheter 220 may not be used. For example, a pulse oximeter may be placed on a finger of patient 210 to monitor the pulse of patient 210 instead of using catheter 220.

Figure 3:
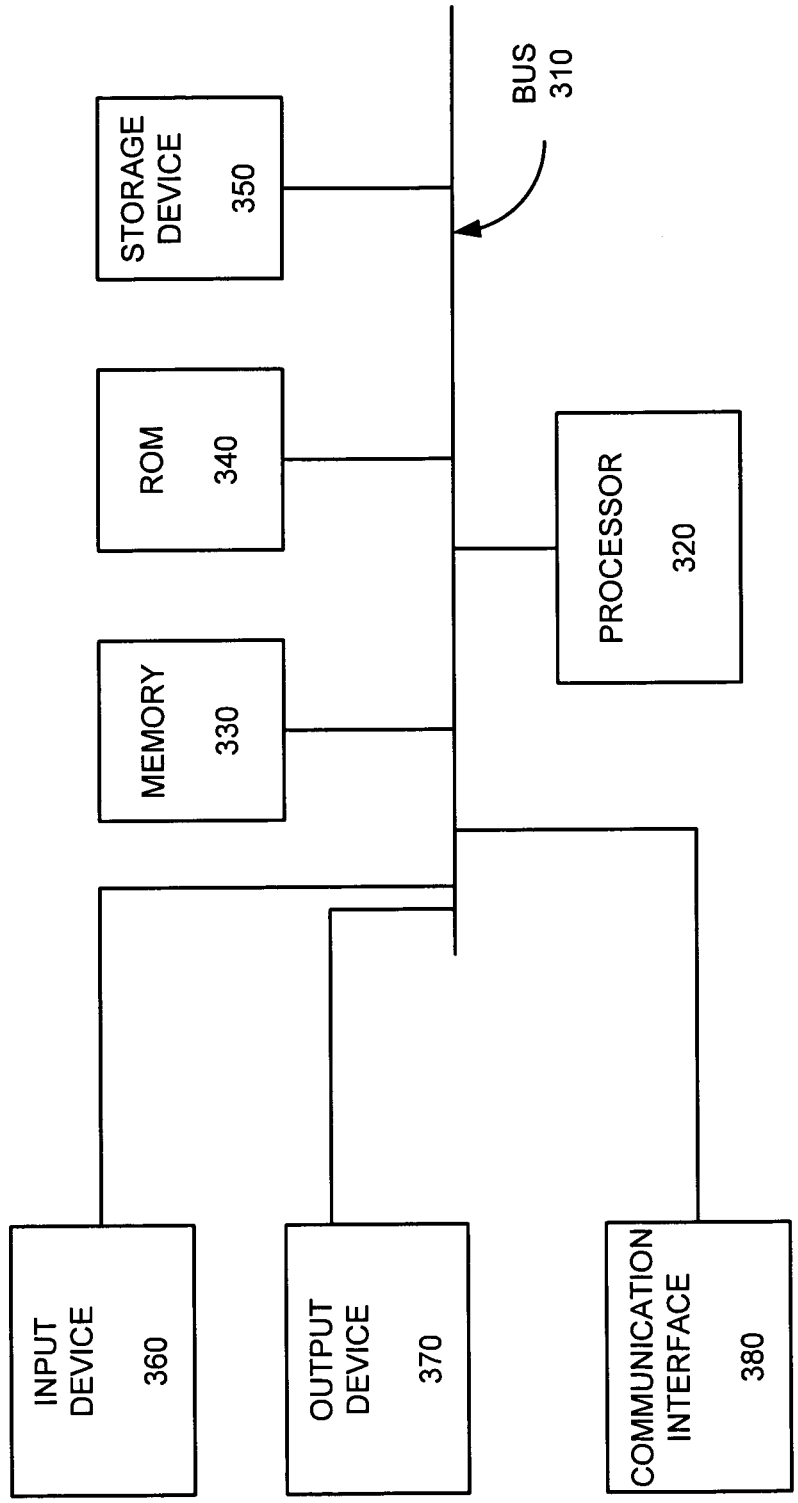
FIG. 3 illustrates an exemplary configuration of the monitoring device of FIG. 2.

FIG. 3 illustrates an exemplary configuration of monitoring device 240. Referring to FIG. 3, monitoring device 240 may include bus 310, processor 320, main memory 330, read only memory (ROM) 340, storage device 350, input device 360, output device 370, and communication interface 380. Bus 310 may include a path that permits communication among the elements of monitoring device 240.

Processor 320 may include a processor, microprocessor, application specific integrated circuit (ASIC), field programmable gate array (FPGA) or processing logic that may interpret and execute instructions. Memory 330 may include a random access memory (RAM) or another type of dynamic storage device that may store information and instructions for execution by processor 320. ROM 340 may include a ROM device or another type of static storage device that may store static information and instructions for use by processor 320. Storage device 350 may include a magnetic and/or optical recording medium and its corresponding drive.

Input device 360 may include a mechanism that permits an operator to input information to monitoring device 240, such as a keyboard, a mouse, a pen, voice recognition and/or biometric mechanisms, etc. Output device 370 may include a mechanism that outputs information to the operator, including a display, a printer, a speaker, etc. Communication interface 380 may include any transceiver-like mechanism that enables monitoring device 240 to communicate with other devices and/or systems. For example, communication interface 380 may include a modem or an Ethernet interface to a LAN. Alternatively, communication interface 380 may include other mechanisms for communicating via a network (not shown).

Monitoring device 240 may perform processing associated with monitoring patient 210, as described in detail below. According to an exemplary implementation, monitoring device 240 may perform these operations in response to processor 320 executing sequences of instructions contained in a computer-readable medium, such as memory 330. A computer-readable medium may be defined as a physical or logical memory device.

The software instructions may be read into memory 330 from another computer-readable medium, such as data storage device 350, or from another device via communication interface 380. The software instructions contained in memory 330 may cause processor 320 to perform processes that will be described later. Alternatively, hard-wired circuitry may be used in place of or in combination with software instructions to implement processes described herein. Thus, implementations described herein are not limited to any specific combination of hardware circuitry and software.

Figure 4:
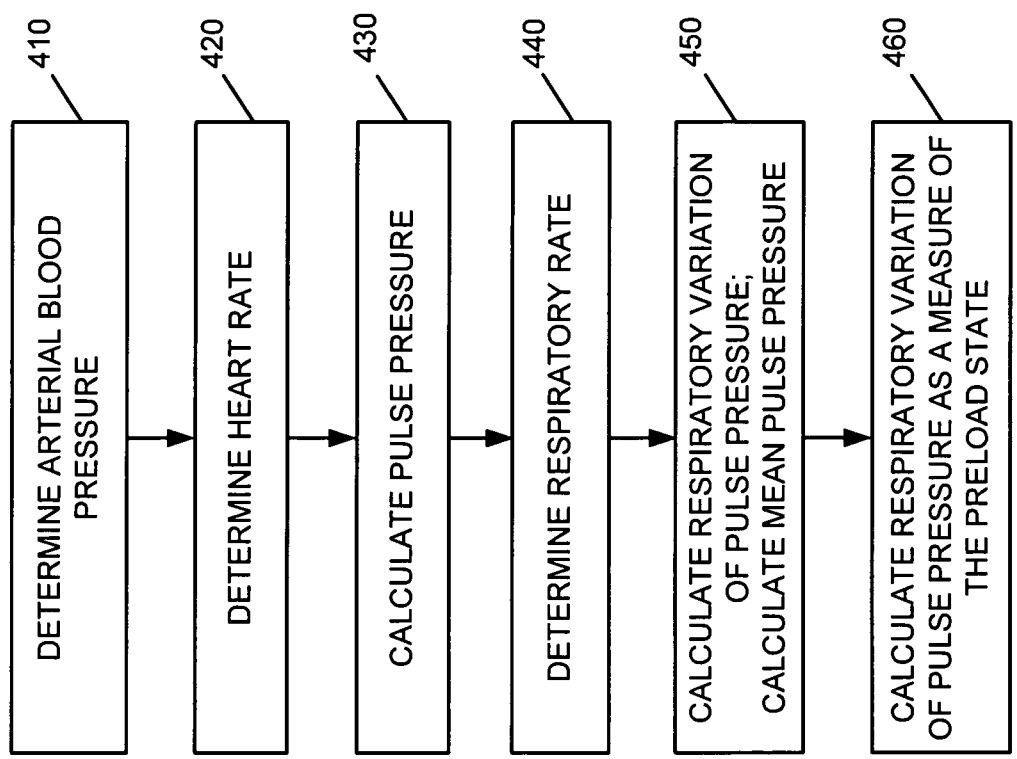
FIG. 4 is a flow diagram illustrating exemplary processing by various devices illustrated in FIG. 2.

FIG. 4 is a flow diagram illustrating exemplary processing associated with monitoring patient 210. In this example, assume that patient 210 is connected to ventilator 230 to assist patient 210's breathing. Catheter 220 may be also inserted into an artery of patient 210 to measure arterial blood pressure. For example, catheter 220 may be inserted into an artery located in a foot or wrist of patient 210. Inserting catheter 220 into a wrist or foot of patient 210, as opposed to inserting catheter 220 into a large artery, such as a femoral artery or axillary artery, enables catheter 220 to be used in a manner that is relatively non-invasive to patient 210. Inserting catheter 220 into an artery in an extremity, such as the wrist or foot, also enables monitoring to be performed on a small child without shredding the vessel, which could cause the loss of a limb. In addition, inserting catheter 220 into the foot or wrist, as opposed to using a Swan-Ganz catheter that must float through the heart to obtain blood pressure measurements, is much safer to patient 210, such as in situations where patient 210 may be in shock. Therefore, catheter 220, consistent with aspects described herein, may be used to obtain blood pressure measurements for virtually any patient 210 (e.g., adult or pediatric), regardless of the physical condition/state of health of patient 210. Catheter 220, as described previously, may include a pressure sensor and/or a transducer that converts the pressure measurements into electrical signals that may be used by monitoring device 240.

Figure 5:
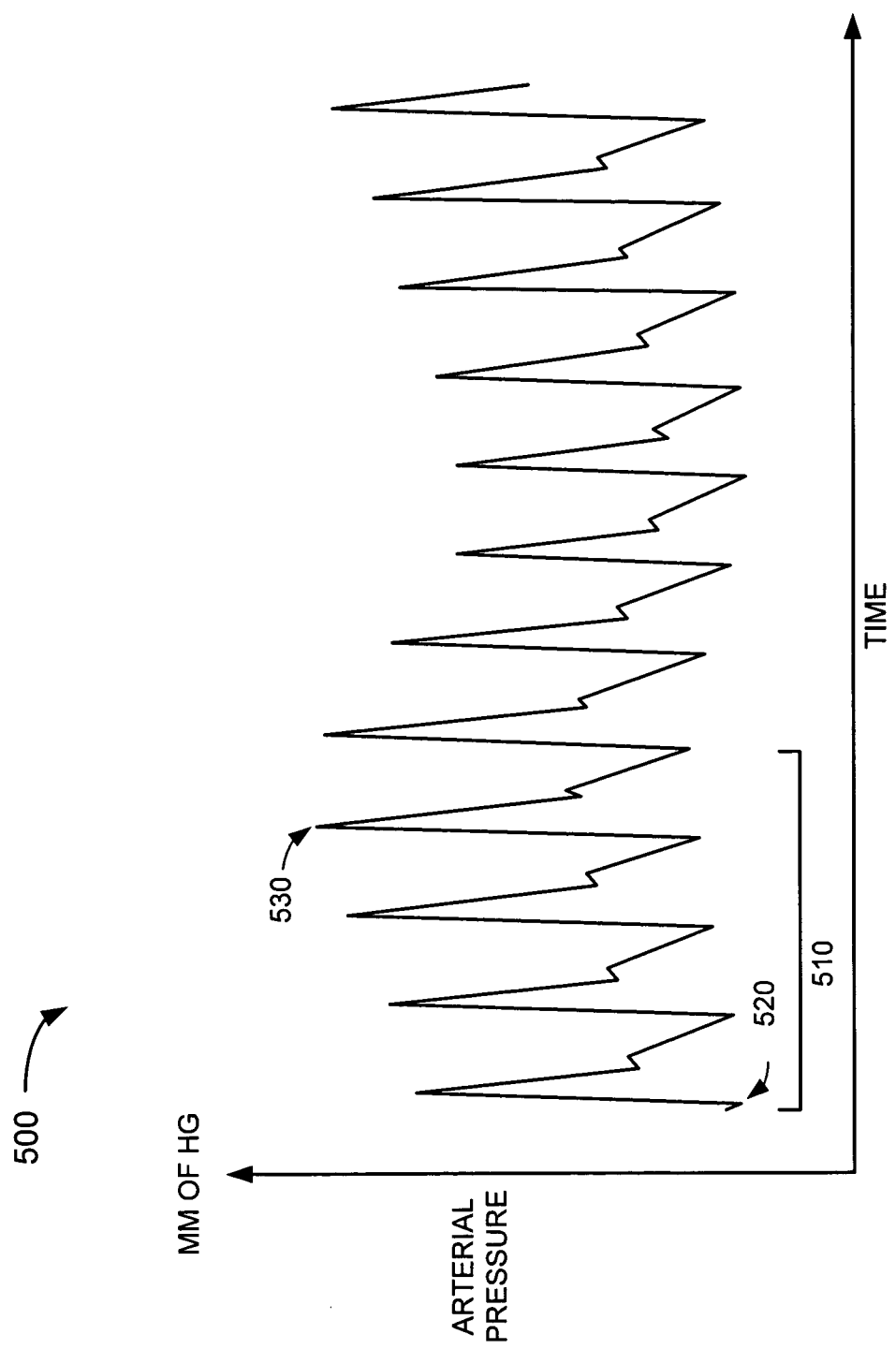
FIG. 5 illustrates an exemplary arterial blood pressure waveform.

Assume that monitoring device 240 is coupled to catheter 220 and receives data from catheter 220. Monitoring device 240 may then determine the arterial blood pressure (ABP) of patient 210 (act 410). For example, catheter 220 may provide electrical signals to monitoring device 240 corresponding to the ABP of patient 210. Processor 320 may sample the ABP at a frequency ranging from, for example, 50-100 times per second (e.g., 50-100 Hz). This sampling frequency satisfies the Nyquist sampling theorem with respect to the ABP of virtually any patient. Other sampling frequencies may alternatively be used. The sampled ABP information may be cached in memory 330. FIG. 5 illustrates an ABP waveform 500 of patient 210 provided via catheter 220. As illustrated, waveform 500 shows that systolic and diastolic pressure varies over a number of cycles. This variation may be used to generate a pulse pressure value, as described in detail below.

Monitoring device 240 may also determine the heart rate of patient 210 (act 420). In one implementation, the heart rate may be determined using an electrocardiogram, a pulse rate monitor or another monitoring device (not shown in FIG. 2). However, in instances in which such heart rate monitoring devices, or other devices from which the heart rate is provided, are not available or not usable due to the condition of patient 210, monitoring device 240 may indirectly derive the heart rate using the ABP waveform (e.g., ABP waveform 500). For example, processor 320 may perform a fast fourier transform (FFT) of the ABP waveform 500 over a window of, for example, 30 seconds. Processor 320 may then determine the heart rate as being equal to the frequency at the maximum amplitude of the FFT. In this manner, processor 320 may convert a time domain ABP waveform into a frequency domain waveform that is used to estimate the heart rate of patient 210.

Processor 320 may also continuously update the heart rate calculation as the ABP waveform changes. For example, processor 320 may calculate the heart rate at least once every five seconds. It should be understood that other periods for updating the heart rate may alternatively be used. Monitoring device 240 may also pre-store information in ROM 340 indicating an allowable range for the heart rate, such as 40 beats per minute (bpm) to 240 bpm. If processor 320 determines that the heart rate of patient 210 is outside this or any other expected range, this may indicate a problem with patient 210 and/or indicate that the data is not reliable. In such cases, monitoring device 240 may output a visual and/or audible alarm via output device 370.

Assume that processor 320 determines that the heart rate is within the allowable range. Monitoring device 240 may calculate the pulse pressure of patient 210 (act 430). The pulse pressure is generally defined as the difference between the systolic and diastolic pressures. In an exemplary implementation, processor 320 may determine the pulse pressure by subtracting the minimum ABP from the maximum ABP over a period of time equal to two times the heart rate period. For example, if the heart rate is 60 bpm (i.e., the heart rate period is one second), processor 320 may subtract the minimum ABP from the maximum ABP over a period of two seconds (i.e., two times the heart rate period of one second). FIG. 5 illustrates an exemplary window or period 510 of two seconds, with point 520 representing the minimum ABP and point 530 representing the maximum ABP over window/period 510. In this case, processor 320 subtracts the pressure value at point 520 from the pressure value at point 530 to obtain the pulse pressure. Processor 320 may calculate the pulse pressure in this manner at least once every heart rate period. That is, in this example, the window for calculating the first pulse pressure may be a two second window 510 depicted in FIG. 5. The next period (i.e., heart rate period) for determining the pulse pressure may overlap with period 510 such that the pulse pressure is calculated at least once every heart rate period, which in this example is one second.

Monitoring device 240 may also determine the respiratory rate of patient 210 (act 440). In an exemplary implementation, the respiratory rate (RR) may be calculated using the pulse pressure measurements. For example, processor 320 may track the pulse pressure over, for example, a 30 second window. Processor 320 may then perform an FFT of the pulse pressure waveform and determine the frequency of the pulse pressure waveform at the maximum amplitude of the FFT. This value may correspond to the respiratory rate of patient 210.

In other instances, monitoring device 240 may determine the respiratory rate using information obtained from ventilator 230. For example, in some instances, ventilator 230 may provide information indicating the mechanically assisted respiratory rate of patient 210.

Processor 320 may also continuously update the respiratory rate calculation over time. For example, processor 320 may calculate respiratory rate at least once every five seconds. It should be understood that other periods for updating the respiratory rate may alternatively be used. Monitoring device 240 may also pre-store information in ROM 340 indicating an allowable range for the respiratory rate, such as 6 breaths per minute to 40 breaths per minute. If processor 320 determines that the respiratory rate is outside of the allowable range, this may indicate a problem with patient 210 and/or indicate that the data is not reliable. In such cases, monitoring device 240 may output a visual and/or audible alarm via output device 370.

Monitoring device 240 may then calculate the respiratory variation of the pulse pressure (act 450). For example, processor 320 may obtain the pulse pressure measurements made over a period of two times the respiratory rate period. For example, if the respiratory rate is 20 breaths per minute (i.e., respiratory rate period of three seconds), processor 320 may obtain the pulse pressure measurements over a period of six seconds (i.e., two times the three second respiratory rate period). Processor 320 may then subtract the minimum pulse pressure ($PP_{min}$) from the maximum pulse pressure ($PP_{max}$) over this period of time. This respiratory variation of pulse pressure (RVoPP) may also be calculated in a continuous manner at least once every 5 seconds. In this case, the RVoPP period for a subsequent period may overlap with the previous period over which the RVoPP calculation is made.

Monitoring device 240 may also calculate the mean pulse pressure (act 450). For example, processor 320 may obtain the pulse pressure measurements made over a period of time equal to two times the respiratory rate and calculate the mean or average pulse pressure (MPP) over this time period. In one implementation, processor 320 may simply sum $PP_{max}$ and $PP_{min}$ over the period and divide this value by two to obtain the MPP. In each case, monitoring device 240 may calculate the MPP in a continuous manner at least once every 5 seconds. Other periods of time for calculating/updating the MPP may alternatively be used.

Monitoring device 240 may then determine the respiratory variation of the pulse pressure as a measure of the preload state of patient 210 (act 460). For example, in one implementation, processor 320 may divide the respiratory variation of the pulse pressure by the mean pulse pressure (i.e., RVoPP/MPP) to generate a value that may be used to indicate a preload state of patient 210. This value or metric may be expressed as a raw number and/or a percentage. In each case, the metric may correspond to the preload state of patient 210.

For example, as described previously with respect to Starling curve 100 (FIG. 1), patients in a condition corresponding to position A will have a marked variation in stroke volume as a function of ventricular preload. Such patients will also have a corresponding variation in respiratory variation of pulse pressure. For example, a patient having a relatively high RVoPP/MPP value, such as greater than 0.13 or 13%, may correspond to a patient that is in a condition located near position A of the Starling curve in FIG. 1. Therefore, if monitoring device 240 determines that patient 210 has a RVoPP/MPP value that meets or exceeds a predetermined value (e.g., 13% in this example), this indicates that patient 210 may benefit by receiving fluid.

Figure 1:
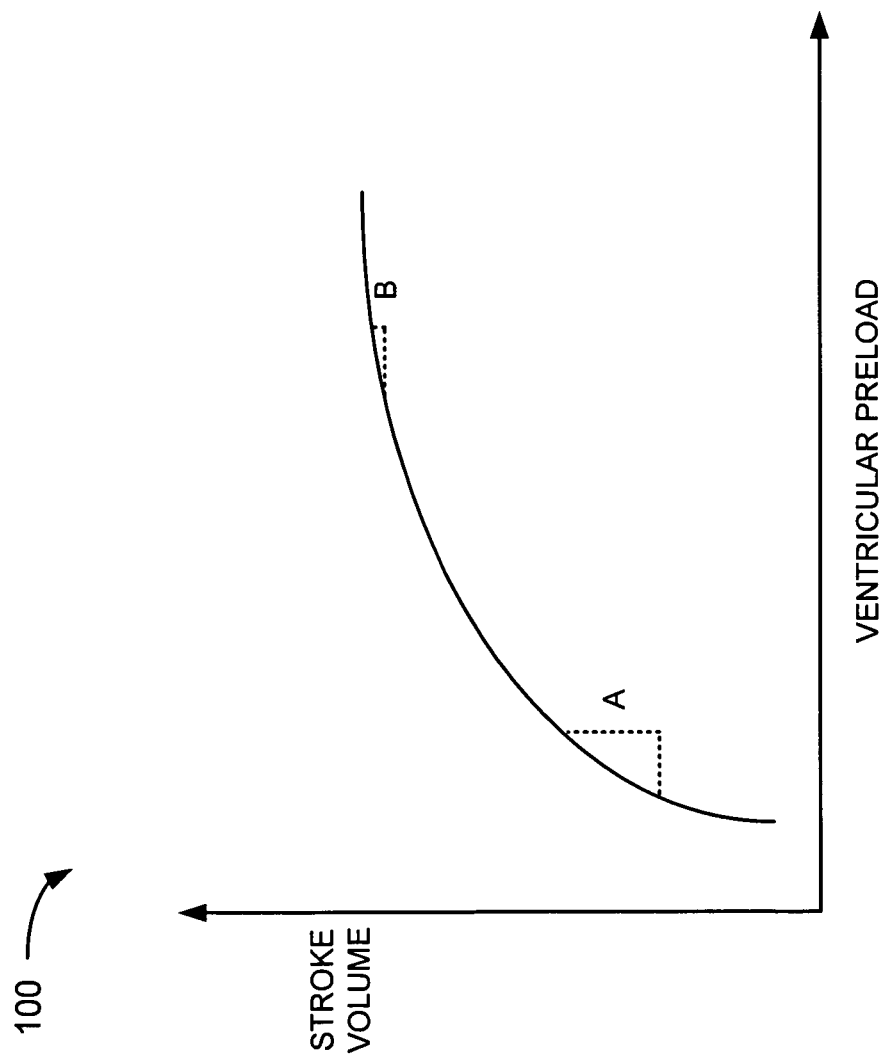
FIG. 1 illustrates an exemplary Starling curve.

In other instances, if RVoPP/MPP determined at act 460 is less than a predetermined value (e.g., 13% in this example), this may indicate that patient 210 is in a condition corresponding to a location near position B of the Starling curve in FIG. 1. In this case, patient 210 may not benefit from receiving fluid. It should be understood that other threshold values associated with RVoPP/MPP may be used as an indication of a preload state of patient 210.

In some implementations, monitoring device 240 may generate a graphical output for display via output device 370. Such a display may include a Starling curve with an indication of where patient 210 falls with respect to the Starling curve. In an one implementation, the point at which patient 210 falls may be highlighted or otherwise indicated on the curve. In other instances, the raw number or percentage may be output for display via output device 370. In each case, medical personnel may view output device 370 to determine the preload state of patient 210.

Monitoring device 240 may continuously update the RVoPP/MPP value in real-time or near real-time. This updated RVoPP/MPP value may be output for display via output device 370. The display may also display a history of values over a period of time either graphically on a graph, such as a Starling curve, or via text. In each case, performing a continuous updating of the metric that may be used to readily identify the current preload state of patient 210 enables medical personnel to quickly determine a course of action that is best suited for patient 210.

In the implementation described above, arterial blood pressure information was provided to monitoring device 240 via catheter 220. In other instances, as described briefly above, a pulse oximeter may be attached to a finger of patient 210 to provide pulse-related data from which a pulse pressure may be determined. For example, a pulse oximeter may be connected to a fingertip of patient 210 to monitor the oxygenation of a patient's blood. Based on the reading associated with the oxygenation of the blood, one of ordinary skill in the art would be able to derive pulse pressure. Respiratory variation of the pulse pressure and mean pulse pressure may then be determined in a manner similar to that described above. In this implementation, measurements made with respect to patient 210 may be done in a totally non-invasive manner via a pulse oximeter.

In each of the implementations described above, respiratory variation of the pulse pressure may be determined to obtain a metric used to estimate the preload state of patient 210, regardless of the heart rate and respiratory rate of the particular patient 210. For example, as described above, the pulse pressure is determined at the frequency of the heart rate and the pulse pressure is then analyzed for variability at the frequency of the respiratory rate, while satisfying the Nyquist sampling theorem. Using such parameters with respect to determining pulse pressure and variability of pulse pressure enables monitoring device 240 to determine a preload state of virtually all patients, including pediatric patients, having an extremely wide range of heart rates and/or respiratory rates.

CONCLUSION

Implementations described herein provide for monitoring respiratory variation of pulse pressure in a continuous manner. Advantageously, the monitoring may be performed in a minimally invasive or non-invasive manner, thereby allowing the monitoring to be performed in virtually any patient, regardless of age and/or condition.

The foregoing description of exemplary implementations provides illustration and description, but is not intended to be exhaustive or to limit the invention to the precise form disclosed. Modifications and variations are possible in light of the above teachings or may be acquired from practice of the invention.

For example, various features have been described above with respect to monitoring device 240 continuously generating a value that indicates a preload state of patient 210. This information has been described as being generated as a function of time. In other instances, the respiratory variation of pulse pressure may be presented as a function of some other variable. For example, in one implementation in which patient 210 has a catheter in his/her neck that provides central venous pressure information, monitoring device 240 may map the respiratory variation of pulse pressure to the central venous pressure. This information may then be used to target a desired central venous pressure using fluid management. The respiratory variation of the pulse pressure may similarly be presented as a function of other parameters associated with the particular patient.

In addition, implementations described above mainly refer to obtaining arterial blood pressure information or pulse oximetry information to obtain a pulse pressure and pulse pressure variation information. In other implementations, any pulse-related information in which the strength of the pulse can be gauged and changes in the strength of the pulse determined over the respiratory cycle may be used.

Further, aspects have been mainly described herein with respect to providing an output (e.g., textual, graphical) that indicates a preload state. In other instances, the preload state may be correlated to an amount of fluid that may be beneficial to patient 210. For example, in some implementations, monitoring device 240 may output parameters indicating how much fluid may be suitable for the patient. It should be understood that any such output from monitoring device 240 would be reviewed and verified by appropriate medical personnel.

In addition, while series of acts have been described with respect to FIG. 4, the order of the acts may be varied in other implementations. Moreover, non-dependent acts may be implemented in parallel.

It will be apparent to one of ordinary skill in the art that various features described above may be implemented in many different forms of software, firmware, and hardware in the implementations illustrated in the figures. The actual software code or specialized control hardware used to implement the various features is not limiting of the invention. Thus, the operation and behavior of the features of the invention were described without reference to the specific software code—it being understood that one of ordinary skill in the art would be able to design software and control hardware to implement the various features based on the description herein.

Further, certain portions of the invention may be implemented as "logic" that performs one or more functions. This logic may include hardware, such as a processor, a microprocessor, an application specific integrated circuit, or a field programmable gate array, software, or a combination of hardware and software.

No element, act, or instruction used in the description of the present application should be construed as critical or essential to the invention unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method, comprising:
 receiving arterial blood pressure data associated with a patient;
 determining a heart rate of the patient using the arterial blood pressure data;
 calculating a pulse pressure of the patient based on a difference between a maximum arterial blood pressure of the patient and a minimum arterial blood pressure of the patient over a period of time equal to at least two times a period of the heart rate of the patient;
 determining a respiratory rate of the patient;
 calculating, using a processor, a respiratory variation of the pulse pressure of the patient based on a difference between a maximum pulse pressure of the patient over a first period of time equal to at least two times a period of the respiratory rate of the patient and a minimum pulse pressure of the patient over the first period of time; and
 calculating a first value by dividing the respiratory variation of the pulse pressure by a mean pulse pressure of the patient,
 wherein the determining a respiratory rate of the patient comprises:
 performing a fast fourier transform of the pulse pressure of the patient calculated over a period of time.

2. The method of claim 1, further comprising:
 determining a ventricular preload state of the patient based on the first value.

3. The method of claim 1, further comprising:
 updating the first value in a continuous manner; and
 outputting updated first values.

4. A method, comprising:
 receiving arterial blood pressure data associated with a patient;
 determining a heart rate of the patient using the arterial blood pressure data;
 calculating a pulse pressure of the patient based on a difference between a maximum arterial blood pressure of the patient and a minimum arterial blood pressure of the patient over a period of time equal to at least two times a period of the heart rate of the patient;
 determining a respiratory rate of the patient;
 calculating, using a processor, a respiratory variation of the pulse pressure of the patient based on a difference between a maximum pulse pressure of the patient over a first period of time equal to at least two times a period of the respiratory rate of the patient and a minimum pulse pressure of the patient over the first period of time; and calculating a first value representing a preload state of the patient based on the respiratory variation of the pulse pressure and a mean pulse pressure of the patient, wherein the determining a heart rate of the patient comprises:

performing a fast fourier transform of the arterial blood pressure data over a period of time, determining a maximum amplitude of the fast fourier transform, and identifying the heart rate as being equal to a frequency at the maximum amplitude of the fast fourier transform.

5. The method of claim 1, wherein the receiving arterial blood pressure data comprises:

receiving arterial blood pressure data from a catheter inserted into a wrist or foot of the patient.

6. The method of claim 1, wherein:

the calculating a pulse pressure comprises calculating the pulse pressure at a frequency of the heart rate of the patient, and the calculating a respiratory variation of the pulse pressure comprises calculating the respiratory variation of the pulse pressure at a frequency of the respiratory rate of the patient.

7. A monitoring device, comprising: logic comprising a processor configured to:

receive arterial blood pressure information associated with a patient, determine a heart rate of the patient, calculate a pulse pressure of the patient by subtracting a minimum arterial blood pressure of the patient from a maximum arterial blood pressure of the patient over a first period of time based on the heart rate of the patient, wherein the first period of time is equal to two times a period of the heart rate of the patient, determine a respiratory rate of the patient, calculate a respiratory variation of the pulse pressure over a second period of time based on the respiratory rate of the patient, wherein the second period of time is equal to two times a period of the respiratory rate of the patient, and generate a first value by dividing the respiratory variation of the pulse pressure by an average pulse pressure of the patient determined over the second period of time, wherein the logic is further configured to:

calculate the pulse pressure at a frequency of at least a frequency of the heart rate, and calculate the respiratory variation of the pulse pressure at least once every five seconds.

8. The monitoring device of claim 7, further comprising:

an output device configured to display the first value, and wherein the logic is further configured to:

update the first value in a real-time or near real-time manner.

9. The monitoring device of claim 7, wherein the first value corresponds to a preload state of the patient.

10. The monitoring device of claim 7, further comprising:

an input device configured to receive the arterial blood pressure information via a catheter inserted into a foot or wrist of the patient and forward the arterial blood pressure information to the logic.

11. The monitoring device of claim 7, wherein the logic is further configured to sample arterial blood pressure information from the patient at a frequency of at least 50 times per second.

12. The monitoring device of claim 7, further comprising:

an output device configured to display a stroke volume versus preload state curve and highlight a point on the curve corresponding to the first value.

13. A non-transitory tangible computer-readable medium having stored thereon sequences of instructions which, when executed by at least one processor, cause the at least one processor to:

receive arterial blood pressure information associated with a patient;

determine a heart rate of the patient based on the arterial blood pressure information;

calculate a pulse pressure of the patient, at a frequency of at least a frequency of the heart rate, based on a maximum arterial blood pressure of the patient and a minimum arterial blood pressure of the patient over a first period of time;

determine a respiratory rate of the patient;

calculate a respiratory variation of the pulse pressure over a second period of time, wherein the second period of time is equal to approximately two times a period of the respiratory rate of the patient; and generate a first value representing a preload state of the patient based on the respiratory variation of the pulse pressure and an average pulse pressure of the patient, wherein when determining a heart rate of the patient, the instructions cause the at least one processor to:

perform a fourier transform of the arterial blood pressure information over a first window of time, determine a maximum amplitude of the fourier transform, and identify the heart rate as being equal to a frequency at the maximum amplitude of the fourier transform.

14. The non-transitory tangible computer-readable medium of claim 13, wherein when generating a first value, the instructions cause the at least one processor to divide the respiratory variation of the pulse pressure by the average pulse pressure, the instructions further including instructions for causing the at least one processor to:

output the first value to a display; and update the first value in a continuous manner based on the received arterial blood pressure information.

15. The non-transitory tangible computer-readable medium of claim 13, wherein when calculating a respiratory variation of the pulse pressure, the instructions cause the at least one processor to:

subtract a minimum pulse pressure determined over the second period of time from a maximum pulse pressure determined over the second period of time.

16. The non-transitory tangible computer-readable medium of claim 13, wherein when determining a respiratory rate of the patient, the instructions cause the at least one processor to:

perform a fourier transform of the pulse pressure over a second window of time.

17. The non-transitory tangible computer-readable medium of claim 13, wherein the first period of time is equal to approximately two times a period of the heart rate of the patient.

18. The non-transitory tangible computer-readable medium of claim 13, further comprising instructions for causing the at least one processor to:

generate a graphical output illustrating ventricular preload versus cardiac output; and highlight the first value on the graphical output.

19. A method, comprising:
receiving pulse-related data associated with a patient;
determining a heart rate of the patient;
calculating a pulse pressure of the patient, using the pulse-related data, over a period of time equal to at least two times a period of the heart rate of the patient;
determining a respiratory rate of the patient;
calculating, using a processor, a respiratory variation of the pulse pressure of the patient based on a difference between a maximum pulse pressure of the patient and a minimum pulse pressure of the patient over a period of time equal to at least two times a period of the respiratory rate of the patient; and
calculating a first value representing a preload state of the patient based on the respiratory variation of the pulse pressure and a mean pulse pressure of the patient,
wherein the determining a respiratory rate comprises:
performing a fast fourier transform of the pulse pressure of the patient calculated over a period of time.

20. The method of claim 19, wherein the receiving pulse-related data comprises receiving information from a pulse oximeter connected to the patient.

21. A device, comprising:
means for receiving at least one of arterial blood pressure information or pulse oximetry information associated with a patient;
means for determining a heart rate of the patient;
means for calculating a pulse pressure of the patient based on the arterial blood pressure information or the pulse oximetry information over a first period of time based on the heart rate of the patient, wherein the first period of time is equal to approximately two times a period of the heart rate of the patient;
means for determining a respiratory rate of the patient;
means for calculating a respiratory variation of the pulse pressure over a second period of time based on the respiratory rate of the patient, wherein the second period of time is equal to at least two times a period of the respiratory rate of the patient;
means for generating a first value representing a preload state of the patient based on the respiratory variation of the pulse pressure and an average pulse pressure of the patient determined over the second period of time; and
means for outputting the first value, wherein the means for determining a respiratory rate comprises:
means for performing a fast fourier transform of the pulse pressure of the patient calculated over a period of time.

22. A monitoring device, comprising:
a display;
an input device configured to receive patient-related data; and
logic configured to:
  receive at least some of the patient-related data from the input device,
  determine a heart rate of the patient,
  determine pulse pressure of the patient over a first period of time based on the patient-related data, wherein the first period of time is equal to approximately two times the heart rate of the patient,
  calculate a respiratory variation of the pulse pressure of the patient over a second period of time equal to at least two times a period of the respiratory rate of the patient,
  generate a first value by dividing the respiratory variation of the pulse pressure of the patient by a mean pulse pressure of the patient,
  output the first value to the display, and
  repeat the determining, calculating, generating and outputting over a period of time in a real-time or near real-time manner,
wherein the logic is further configured to:
  calculate the pulse pressure at a frequency of at least a frequency of the heart rate, and
  calculate the respiratory variation of the pulse pressure at least once every five seconds.

* * * * *